United States Patent [19]
Artiss et al.

[11] Patent Number: 5,215,922
[45] Date of Patent: Jun. 1, 1993

[54] METHOD AND COMPOSITIONS FOR THE DETERMINATION OF SERUM CALCIUM USING AERSENAZO III

[75] Inventors: Joseph D. Artiss, Windsor, Canada; Bradley R. Morgan, Champaign, Ill.; Bennie Zak, West Bloomfield, Mich.

[73] Assignee: The Board of Governors of Wayne State University, Detroit, Mich.

[21] Appl. No.: 831,190

[22] Filed: Feb. 5, 1992

[51] Int. Cl.$^5$ .................. G01N 31/00; G01N 33/20
[52] U.S. Cl. ........................... 436/16; 436/17; 436/74; 436/79; 436/164; 436/166; 252/408.1; 422/82.09
[58] Field of Search .............. 436/74, 79, 164, 166, 436/17, 8, 16; 252/408.1; 422/82.09

[56] References Cited

U.S. PATENT DOCUMENTS

| | | | |
|---|---|---|---|
| 4,626,511 | 12/1986 | Artiss | 436/8 |
| 4,871,679 | 10/1989 | Tanaka et al. | 436/79 |
| 5,057,435 | 10/1991 | Denney | 436/79 |

OTHER PUBLICATIONS

Michaylova, V. & P. Ilkova, Anal Chim Acta 53:194-198 (1971).
Michaylova, V., et al., Anal Chim Acta 68:73-82 (1974).
Savvin, S. B., Doklady Akad Nauk USSR 127:1231-1234 (1959).
Grindler E. M., et al., Am J. Clin Pathol 58:376-382 (1972).
Willard, H. H., et al., Advanced Quantitative Analysis, 3rd ed. N.Y.: D. Van Nostrand (1943).
Sandell, E. B., Colorimetric Determination of Traces of Metals, 3rd ed. N.Y.: Interscience Publishers (1959).
Lamkin, E. G., et al., Anal Chem 37:1029-1031 (1965).
Giacola, G. P. & Krasner, Amer. J. Med. Technol. 45:767-768 (1979).
Kendrick, N., et al., Anal Biochem 83:433-450 (1977).
Sharma, A., et al., Microchem J 39:86-93 (1989).
Henry, R. J., et al., Clinical Chemistry, principles and techniques, 2nd ed. N.Y., Harper & Row (1974).
Ogan, K., et al., Anal Biochem 96:70-76 (1979).
Koch, T. R., et al., Bilirubin, total & conjugated, modified Jendrassik-Grof method. In Faulkner, ed. Selected methods for the small clinical chemistry Lab. Washington, D.C.: American Assocation for Clinical Chemistry (1982).
Artiss, J., et al., Trands in Anal Chem 6:185-191 (1987).
Musiala, T. S., et al., Dubin. Clin Chem 23:1121 (1977).
Epstein, E., et al., Ann Clin Lab Sci 2:244 (1972).
Helenius, A., et al., Biochemistry 10:2452 (1971).
Moorjani, S., et al., Clin Chem. Acta 77:21 (1977).
Zeppazaur, M., et al., Biochim Biophys Acta 94:581 (1965).
Morgan, B., et al., Enzymic clearing for the determination of serum calcium. Microchem J, 44:15-24 (1991).
Sharma, A., et al., Clin Chim Acta 147:7-14 (1985).
Artiss, J. D., et al., Clin Chim Acta 156:151-156 (1986).
Sharma, A., et al., J. Clin Chem Clin Biochem 24:571-575 (1986).

Primary Examiner—James C. Housel
Assistant Examiner—N. Bhat
Attorney, Agent, or Firm—Ian C. McLeod

[57] ABSTRACT

A colorimetric, particularly spectrophotometric, method and compositions for determining calcium levels in blood serum in the presence of magnesium and other serum ions is described. The method uses an aqueous composition with a pH between about 7.5 and 10 with arsenazo III to complex calcium and a hydroxyquinoline selected from the group consisting of 8-hydroxyquinoline and 8-hydroxyquinoline-5-sulfonate to complex magnesium. Lipase and a cyclodextrin can be used as reagents to clear triglycerides in the serum which can provide turbidity and false results in some instances. The method is particularly useful for human serum.

21 Claims, 8 Drawing Sheets

METHOD AND COMPOSITIONS FOR THE DETERMINATION OF SERUM CALCIUM USING AERSENAZO III

BACKGROUND OF THE INVENTION (1) Field of the Invention

The present invention relates to a method for the colorimetric, particularly spectrophotometric, determination of calcium in serum, particularly human blood serum, using arsenazo III as an indicator which complexes with calcium to develop a color along with a hydroxyquinoline which binds magnesium in the serum without forming a colored complex. In particular, the present invention uses an alkaline aqueous reagent which contains 8-hydroxyquinoline or preferably 8-hydroxyquinoline sulfonic acid (also known as 8-hydroxyquinoline sulfonate) which complexes with magnesium so that it is non-reactive with arsenazo III.

(2) Prior Art

Arsenazo III (ASA III) has been used as a selective ligand for the colorimetric determination of several metals (Michaylova, V. and P. Ilkova, Anal Chim Acta 53:194–198 (1971); Savvin, S. B., Talanta 8:673–685 (1961); Michaylova, V. and L. Yoroukova, Anal. Chim. Acta 68:73–82 (1974); and Savvin, S. B., Doklady Akad Nauk USSR 127:1231–1234 (1959)). However, in the clinical laboratory its most common application has been limited to the determination of serum calcium. Since ASA III was first used by Michaylova and Ilkova (Michaylova V. and P. Ilkova, Anal Chim Acta 53:194–198 (1971)), these colorimetry calcium determinations have been performed at an acidic pH because of the greater selectively by ASA III for calcium over magnesium under acidic conditions, where the latter has been shown to be a major interfering ion in serum in other calcium assays involving alkaline reactions (Connerty, H. V. and A. R. Briggs, Am J Clin Path 45:290–296 (1966)). The alkaline pH region has not been used for serum determinations of calcium even though the molar absorptivity of ASA III increases with pH with a maximum value occurring at pH 9 (Michaylova V. and P. Ilkova, Anal Chim Acta 53:194–98 (1971)).

In the past, 8-hydroxyquinoline (8HQ) has been used as a masking agent for magnesium in methylthymol blue and orthocresolphthalein complexone based calcium reagents (Connerty H. V. and A. R. Briggs, Am J Clin Path 45:290–296 (1966); and Grindler, E. M. and J. D. King Am J Clin Pathol 58:376–382 (1972)), both tests being carried out in alkaline aqueous solutions. Studies have shown that the masking of magnesium by 8HQ is not always complete in these tests. In addition, the interaction of magnesium with 8HQ can also cause high results for calcium in comparison to more definitive methods (Connerty H. V. and A. R. Briggs, Am J Clin Path 45:290–296 (1966); and Grindler, E. M. and J. D. King, Am J Clin Pathol 58:376–382 (1972)).

8HQ was originally used as analytical reagent for magnesium in procedures where magnesium 8-hydroxyquinolate was first precipitated either in ammoniacal solutions or sodium hydroxide solutions containing tartrate at alkaline pHs ranging from 9.5 to 12.6. The hydroxyquinolate precipitate was then determined colorimetrically (Willard, H. H. and H. Diehl, Advanced Quantitative Analysis, 3rd ed. New York: D. Van Nostrand (1943); and Sandell, E. B., Colorimetric Determination of Traces of Metals, 3rd ed. New York: Interscience Publishers (1959)). Under conditions that the orthocresolphthalein complexone and methylthymol blue procedures are performed, the reported precipitates of magnesium quinolate have not been found, probably because the solubility maximum of the magnesium quinolate is not exceeded by the levels of magnesium encountered in serum with these reagents.

An early study (Lamkin, E. G. and M. B. Williams, Anal Chem 37:1029–1031 (1965)) provided an indirect method for determining calcium by reacting calcium and magnesium with ASA III to get a total absorbance and then removing the calcium absorbance by binding it with [ethylene bis (oxyethylene-nitrilo)] tetraacetic acid. This test involves multiple steps. A more sensitive ASA III calcium reagent would be particularly useful in applications requiring small sample volumes such as automated instrumentation and in laboratories servicing a large neonatal or geriatric population. In addition, since it has been reported that hypertriglyceridemia can cause aberrant elevated results for serum calcium when assayed spectrophotometrically (Giacola, G. P. & Krasner, Amer. J. Technol 45 767–768 (1979)), an improved reagent that would permit the on-line measurement of calcium in samples that are turbid enough to cause the light-scatter artifacts is needed.

OBJECTS

It is therefore an object of the present invention to provide a method and compositions for determining serum calcium in the presence of serum magnesium. In particular, it is an object of the present invention to provide a method using arsenazo III as the complexing agent in a system which completely blocks the complexing of magnesium with arsenazo III to produce a false reading. Further still, it is an object of the present invention to provide a method and compositions which are simple and economical. These and other objects will become increasingly apparent by reference to the following description and the drawings.

BRIEF DESCRIPTION OF THE DRAWINGS

FIGS. 2A, 2B, 2C and 2D are graphs showing the spectra of ASA III-Mg complexes using reagent containing various concentrations of 8HQS. FIG. 2A [8HQS]: 0mmol/L; FIG. 2B, [8HQS]: 3 mmol/L; FIG. 2C [8HQS]: i mmol/L; FIG. 2D [8HQS]: 5 mmol/L (dotted lines) a. [Mg]: 1 mmol/L; b. [Mg]: 3 mmol/L; c. [Mg]: 5 mmol/L.

FIGS. 3A and 3B are graphs wherein FIG. 3A shows the spectra of pure calcium standards using reagent lacking the masking agent 8HQS. FIG. 3A shows calcium containing magnesium.

FIGS. 4A and 4B are graphs, wherein 4A shows the spectra of calcium standards using reagent containing 8HQS at 5 mmol/L.

FIG. 5A shows a greater absorbance for the same amount of calcium.

FIGS. 6A, 6B and 6C show various spectra demonstrating the utility of lipase and α-cyclodextran to eliminate the turbidity caused by hypertriglyceridemia.

FIG. 6° C. shows the spectra of the 2.50 mmol/L calcium standard contaminated with triglyceride as intralipid as in the left panel, now after 8 minutes incubation at 37° C. [TG]: 40 g/L.

GENERAL DESCRIPTION

The present invention relates to a method for a colorimetric determination of an amount of calcium in the presence of magnesium in a sample with arsenazo III as a reagent the improvement which comprises: providing an aqueous composition at a pH between about 7.5 and 10 containing arsenazo III and a hydroxyquinoline selected from the group consisting of 8-hydroxyquinoline and 8-hydroxyquinoline-5-sulfonate in amounts such that the magnesium in the sample can complex with the hydroxyquinoline which is colorless and the calcium in the sample can complex with the arsenazo III; adding the composition to the sample, wherein the calcium complex of arsenazo III produces a color with an intensity which is a function of the amount of calcium in the presence of the magnesium complexed with the hydroxyquinoline; and (c) colorimetrically determining the amount of calcium in the sample.

The present invention also relates to a composition for determining calcium colorimetrically in the presence of magnesium which comprises in admixture in an aqueous solution having a pH between about 7.5 and 10: arsenazo III; and a hydroxyquinoline selected from the group consisting of 8-hydroxyquinoline and 8-hydroxyquinoline-5-sulfonate wherein the composition contains between about 0.001 and 0.08 percent by weight of the arsenazo III and between about 0.01and 1.1 percent by weight of the hydroxyquinoline and wherein calcium in the sample complexes to form a color with arsenazo III and magnesium in the sample complexes with the hydroxyquinoline to form a colorless complex.

The present invention relates to an analytical method for the determination of serum calcium in which the ligand used is arsenazo III in an alkaline medium. The choice of pH differs from the prior art procedures which are all carried out in a slightly acid medium. The advantage of the acid assay is that there is no interference from magnesium. However, its disadvantage is that this pH dependent reaction is suboptimal for calcium at an acid pH resulting in a molar absorptivity of 13,787 L/mol cm when compared maximum of 26,574 L/mol cm for an alkaline pH (9.0 pH).

The improved method also includes a clearing procedure for the hypertriglyceridemic condition by incorporating a cyclodextrin as the host for the guest non-esterified fatty acids liberated by a lipase. Water soluble 8-hydroxyquinoline or preferably 8-hydroxyquinoline sulfonate is used as the magnesium complexing agent. 8-hydroxyquinoline is difficult to solubilize in the alkaline solution used in the present invention and thus is not preferred. The use of 8-hydroxyquinoline sulfonate simplifies preparation and concentration control of magnesium because it is more soluble. 8-hydroxyquinoline sulfonate is a superior complexing agent when all analysis factors are considered and is preferred.

The serum is preferably, although not necessarily, human. It is centrifuged to remove blood cells. Various mammalian blood serums can be tested using the reagents of the present invention. Typically in human serum, calcium is present in amounts between about 1.5 and 3.75 mmole per liter. The norm is about 2.1 to 2.65 mmol per liter. Various metal ions occur in serum such as magnesium (0.65–1.05 mmol/L), copper (11.0–24 $\mu$mol/L), zinc (10.0–17.6 $\mu$mol/L) and iron (7.16–28.6 $\mu$mol/L), which must not be interfering.

Various buffers can be used to provide and maintain the alkaline pH. A boric acid, potassium chloride and sodium hydroxide mixture can be used. Other buffers are for instance:

| Buffer | pH Range |
| --- | --- |
| 2-amino-2-methyl-1,3-propanediol in aqueous HCl | 7.8–10.0 |
| Sodium Barbital in aqueous Sodium Acetate | 2.6–9.4 |
| Sodium Barbital in aqueous HCl | 6.8–9.6 |
| Borax in aqueous HCl | 7.6–9.24 |
| Ethanolamine in aqueous HCl | 8.6–10.4 |
| Glycine in aqueous Sodium Hydroxide | 8.8–10.8 |
| Tris in aqueous HCl | 7.2–9.0 |

These are to be considered as examples. Any buffer that does not bind calcium and has the appropriate pH would be acceptable.

The buffers must not contain calcium, since it would void the results of the test.

If the serum contains triglycerides, they can be hydrolyzed by lipases to fatty acids and glycerol. This prevents turbidity in the aqueous solution which interferes with the results Usually the serum has relatively low levels of triglycerides and thus there is no interference. Where a lipase is used, the fatty acids can be bound in the serum using a cyclodextrin. Alpha cyclodextrin is preferred. There are many cyclodextrins which are known and which can be used.

It is preferred that the determination of the colorimetric complex be made at about 625 to 675 nm, with 650 nm being preferred. At pH 7.5 to 10 these spectra provide peak quantitation of the calcium levels and the hydroxyquinoline transfers the magnesium.

The preferred amount of the hydroxyquinoline is between about 0.01 and 1.1 percent by weight of the composition and in an amount sufficient to complex the magnesium. The preferred amount of the arsenazo III is between about 0.00% and 8 percent by weight of the composition. The preferred weight ratio of arsenazo III to hydroxyquinoline is preferably about 0.071.

The lipase is used in an amount between about 50 kilounits (KU) and 10,000 KU sufficient to clear the triglycerides.

It is preferred to use a dispersing agent in the composition to prevent coagulation of the reagents which could provide false positive absorbance. Triton X-100 TM sold by Sigma Chemical, St. Louis, Mo. is preferred which is a p-isooctylphenyl ether having the general formula:

where n is between 9 and 10. Preferably between about 0.005 and 0.5 percent by weight of the composition is used. This weight ratio of the ether to arsenazo III is preferably about 0.16.

The inclusion of lipase in the composition to quickly convert triglyceride to non-esterified fatty acids and glycerol plus the addition of alpha-cyclodextrin to act as a host molecule for the liberated fatty acids, potential soap formers, particularly provides on-line usefulness of the composition for automated methods. Because excessive triglycerides are a common cause of light scattering problems (U.S. Pat. No. 4,626,511 to Artiss et al), it is worthwhile to include the clearing ingredients in the composition (Sharma, A., et al., Microchem J 39:86-93 (1989)).

SPECIFIC DESCRIPTION

Materials and Methods

A Model 25 automatic scanning spectrophotometer (Beckman Instruments, Inc., Fullerton, Calif.) was used throughout the study. A Digiflex Automatic Pipette (Micromatic Systems Inc., Horsham, Pa.) was used for all pipetting.

Chemicals

Arsenazo III, bovine albumin, bilirubin, Triton X-100, alpha-cyclodextrin and 8-hydroxyquinoline-5-sulfonate were obtained from Sigma Chemical Co., St. Louis, Mo.; calcium, copper, iron, magnesium and zinc atomic absorption standards were obtained from Fisher Chemical Co., Fairlawn, N.J.; boric acid, potassium chloride, sodium hydroxide and 8-hydroxyquinoline were obtained from Mallinckrodt Chemical Co., Phillipsburg, Pa.; lipase (glycerol ester hydrolase, E.C. 3.1.1.3) was provided by Genencor International, Rochester, N.Y.

All standards were prepared by diluting the desired atomic absorption standard with water to give the desired metal concentrations.

Calcium standards from New England Research Laboratories, East Providence, R.I. were used for the reproducibility and comparison studies.

Beckman Decision control serums, Beckman Instruments Inc., Brea, Calif. were used for the reproducibility studies.

Preparation of reagent

The reagent was prepared in boric acid-KCl-NaOH buffer, 0.05 mol/L, pH 8.5 (Henry, R. J., et al., Clinical Chemistry, principles and techniques, 2nd ed. New York, Harper and Row (1974)) to contain per liter arsenazo III, 0.08 g; 8-hydroxyquinoline-5-sulfonate, 1.13 g; Triton X-1000, 0.5 g.

A separate reagent was also prepared which contained per liter: arsenazo III, 0.1 g; 8hydroxyquinoline-5-sulfonate, 1.13 g; lipase, 1000kU; alpha-cyclodextrin, 2g; Triton X-100, 0.5 g. The lipase chosen was optimal for its activity at pH 8.5. The difference in arsenazo III over the first reagent is due to $Ca^{++}$ contamination in lipase preparation

Procedure

Without clearing

Twenty microliters of sample was added to 2 mL of reagent, incubated at room temperature for 2 minutes, and the absorbance measured at 650 nm against a reagent blank.

With Clearing:

Twenty microliters of sample was added to 2mL of reagent, incubated at 37° C. for 8 minutes, and the absorbance measured at 650 nm against a reagent blank.

EXAMPLE 1

The method was developed to accommodate a sample to reagent ratio of 1:100. The ASA III concentration in the reagent was adjusted so that the dynamic range of the reagent allowed linearity between 0 and 3.75 mmol/L (15 mg/dL) calcium. To effect this, a series of solutions of varying ASA III concentrations were prepared by dissolving the ASA III in buffer at pH 9.0. Determinations were performed with low, normal and high calcium standards (1.25, 2.50 and 3.75 mmol/L) and measured at the peak maximum of 650 nm versus a reagent blank. In this manner, the minimum amount of ASA III required to perform the assay within the above range of calcium concentrations was established In the absence of the masking agent, 8HQS, 0.056 g/L of ASA III concentration was required. However, to insure the maintenance of linearity at upper concentrations, the ASA III concentration was then increased to 0.08 g/L, leaving a generous margin of excess reagent.

Because pH and ionic composition of the buffer are known to have a profound effect on the spectral nature of both uncomplexed and calcium complexed ASA III (Kendrick, N., et al., Anal Biochem 83:433–450 (1977); and Ogan, K. and E. R. Simons, Anal Biochem 96:70–76 (1979)), solutions of ASA III at 0.08 g/L with 8HQS at 5 mmol/L were prepared in buffers ranging from pH 8.0 to pH 9.5 using increments of 0.5 pH units so that the spectra could be studied under varying conditions. FIGS. 1A to 1D present the several sets of spectra showing uncomplexed ASA III blanked versus water (dashed lines) and three calcium standards: 1.25 mmol/L, 2.50 mmol/L and 3.75 mmol/L (solid lines), all measured versus reagent blanks at the several pH levels. The blank absorbance increased in a non-linear fashion with increasing pH. At pH 8.0 the absorbance of the blank at 650 nm was 0.30, and increased at pH 8.5 to 0.40, at pH 9.0, to 0.68 and finally at pH 9.5 to 0.86. The spectra of the sets of standards scanned versus reagent blanks appeared similar, with the absorbance maxima of the two peaks remaining at 650 nm and 600 nm. It is apparent from these FIGS. 1A to 1D that the peak absorbance at 650 nm increased with increasing pH to a maximum at pH 9.0, while beyond that point it decreased. Standard curves for calcium generated at these various pHs were all linear with the slopes reflecting the changing molar absorptivity of 22,803L/mol cm at pH 8.0, 24,980L/mol cm at pH 8.5, 26,574L/mol cm at pH 9.0 and 24,622 at pH 9.5. Since the peak absorbance at 650nm at pH 8.5 was only slightly less (94%) than at pH 9.0, pH 8.5 was chosen as the best compromise (considering the absorptivity as well as absorbance of the blank) at which to carry out the measurement. The added factor for the choice was that the use of pH 8.5 also makes this reagent amenable to the enzymic clearing technology that was previously applied to an acidic ASA III reagent at pH 6.6.

EXAMPLE 2

Since ASA III reacts with magnesium at an alkaline pH, in contrast to the traditional acidic reagent, magnesium had to be masked in this reaction environment. Initially, solutions of 8-hydroxyquinoline (8HQ) having concentrations from 2 mmol/L to 4mmol/L were prepared in buffer without ASA III at pH 8.5. However, solutions of 8HQ having concentrations greater than 4 mmol/L could not be easily prepared because of the low solubility of 8HQ in the aqueous medium. In addition, a fine precipitate appeared in the bottom of the reagent bottle after 3-4 weeks. Therefore, a more water soluble form of 8HQ, 8-hydroxyquinoline-5-sulfonate (8HQS), was tested as the masking agent in the reagent. Solutions of 8-HQS ranging from 1 mmol/L to 5 mmol/L were prepared in buffer without ASA III at pH 8.5 and mixed with magnesium standards ranging from 1 mmol/L to 5 mmol/L and magnesium standards contaminated with calcium within the same molar range. As expected, owing to the greater solubility of the sulfonated compound, no precipitates were seen in the reaction mixtures either with the reagent or with standards containing magnesium as high as 5 mmol/L when examined visually or spectrophotometrically. Then when magnesium was premixed with calcium and tested in this same manner, the mixtures produced identical results. The 8HQS solutions and mixtures of 8HQS with magnesium standard were scanned against water from 500 nm to 700 nm. At 525 nm, the absorbance of the solutions began to increase. At 650 nm, the wavelength of measurement of the ASA III-Ca complex, the absorbances of all of the 8HQS-Mg solutions with or without calcium were insignificant at less than 0.005.

EXAMPLE 3

Figure 1A:
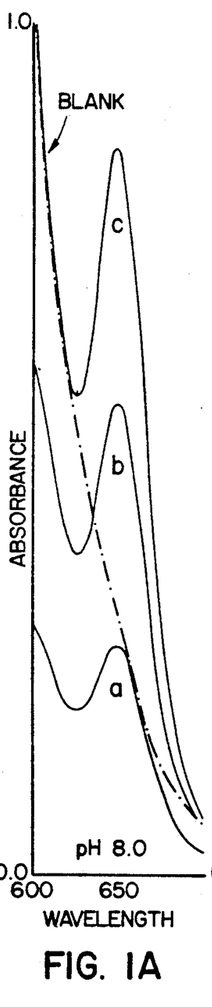
FIGS. 1A, 1B, 1C and 1D are graphs showing the spectra (absorbance vs wavelength) obtained with uncomplexed arsenazo III (dashed lines) blanked versus water and calcium standards at various levels occurring in serum mixed with arsenazo III reagents containing 8-hydroxyquinoline-5-sulfonate (solid lines) blanked versus reagent at different pHs. [ASA III]: 0.08 g/L; and [8HQS]: 5 mmol/L; a. [Ca]: 1.25 mmol/L; b. [Ca]: 2.50 mmol/L; c.[Ca]: 3.75 mmol/L.
Figure 1B:
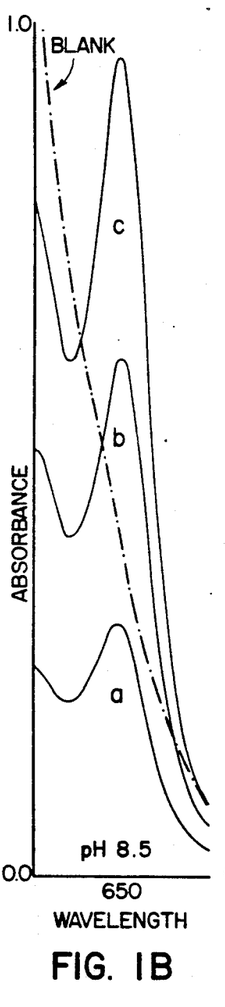
Figure 1C:
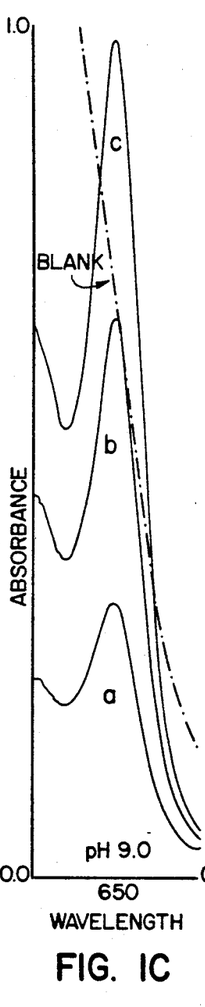
Figure 1D:
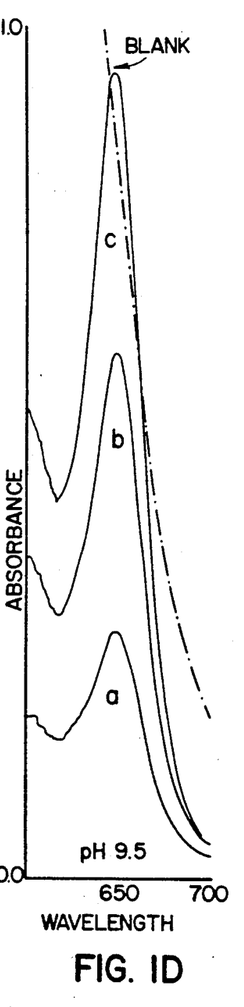
Figure 2A:
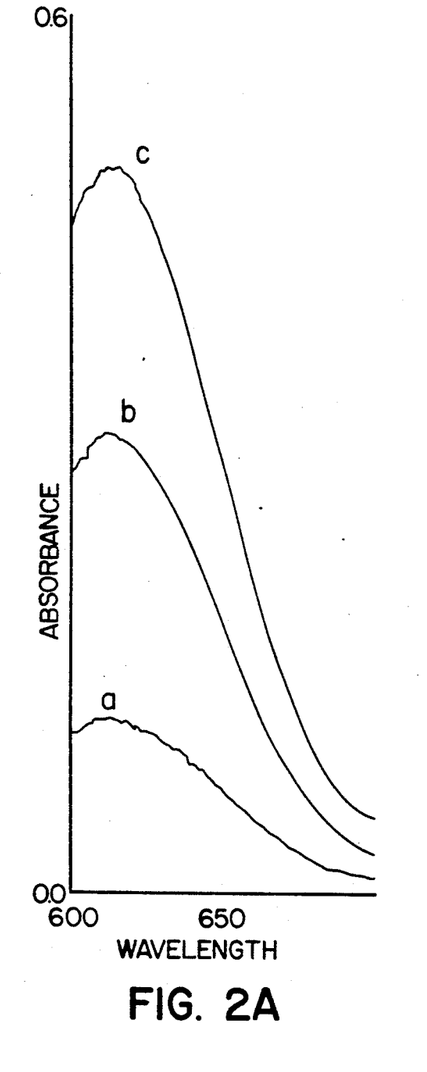
Figure 2B:
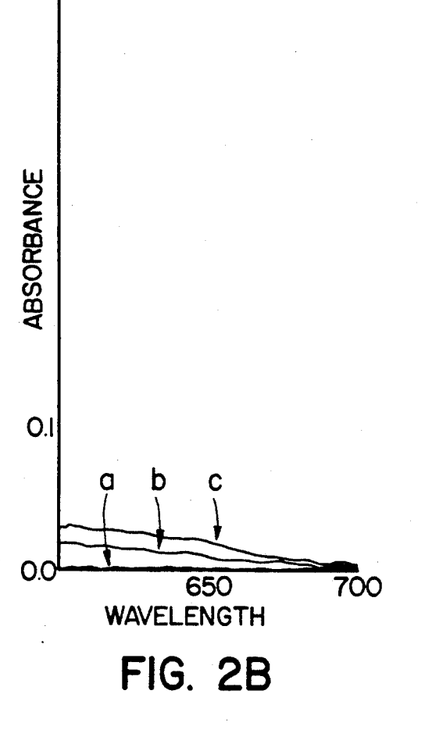
Figure 2C:
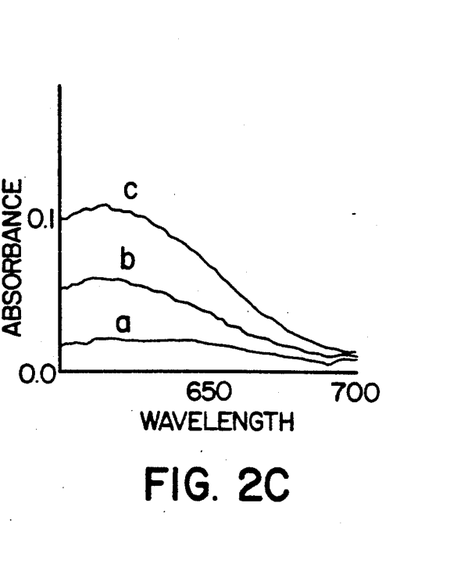
Figure 2D:
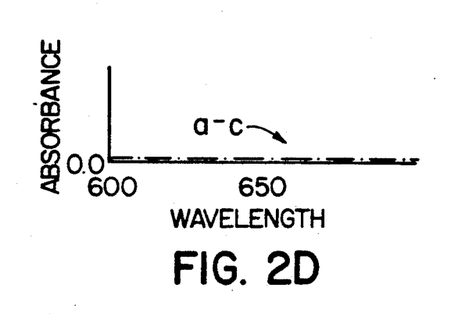

Arsenazo III was then dissolved in each 8HQS solution to give a concentration of 0.08g/L. FIGS. 2A, 2B, 2C and 2D show the spectra of reagent complexed with increasing amounts of magnesium ranging from 0 mmol/L to 5 mmol/L, blanked versus reagent. FIG. 2A shows the spectra of ASA III-Mg complexes in the absence of 8HQS. An absorbance maximum is present at 612nm, which becomes less manifest as the 8HQS concentration increases in the reagent (FIGS. 2B, 2C and 2D). As seen in FIG. 2D by a dashed line, masking was complete when the 8HQS concentration in the reagent was 5 mmol/L.

EXAMPLE 4

Figure 3A:
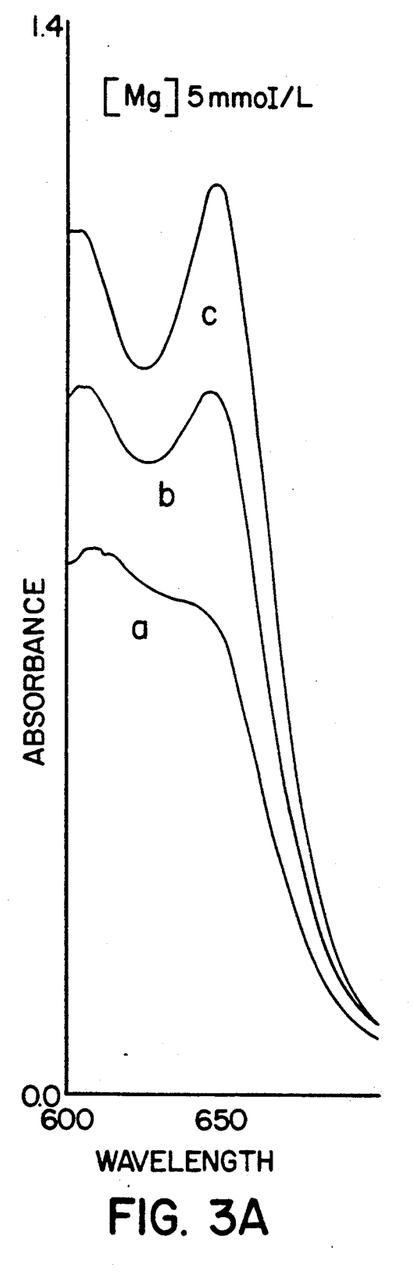
Figure 3B:
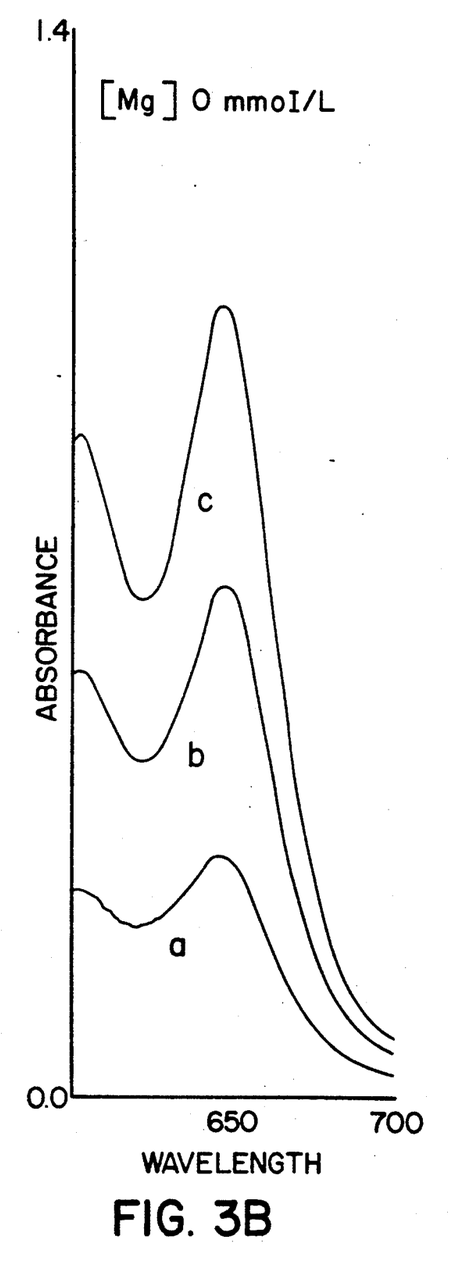
FIG. 3B shows the spectra of pure calcium standards uncontaminated by magnesium at 5 mmol/L using reagent lacking the masking agent [ASA III]: 0.08 g/L; a. [Ca925 mmol/L; b. [Ca]: 2.50 mmol/L; c. [Ca]: 3.75 mmol/L.
Figure 4A:
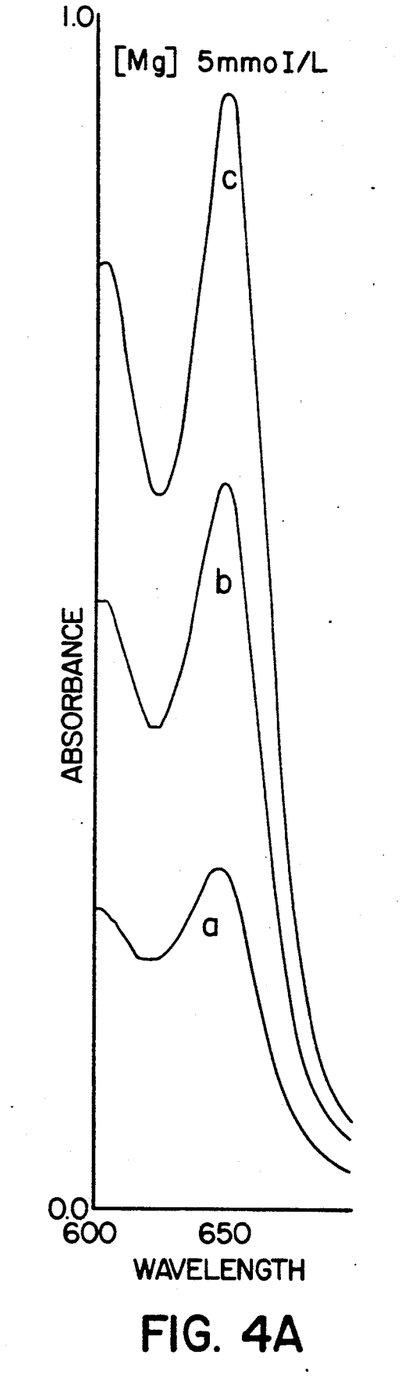
Figure 4B:
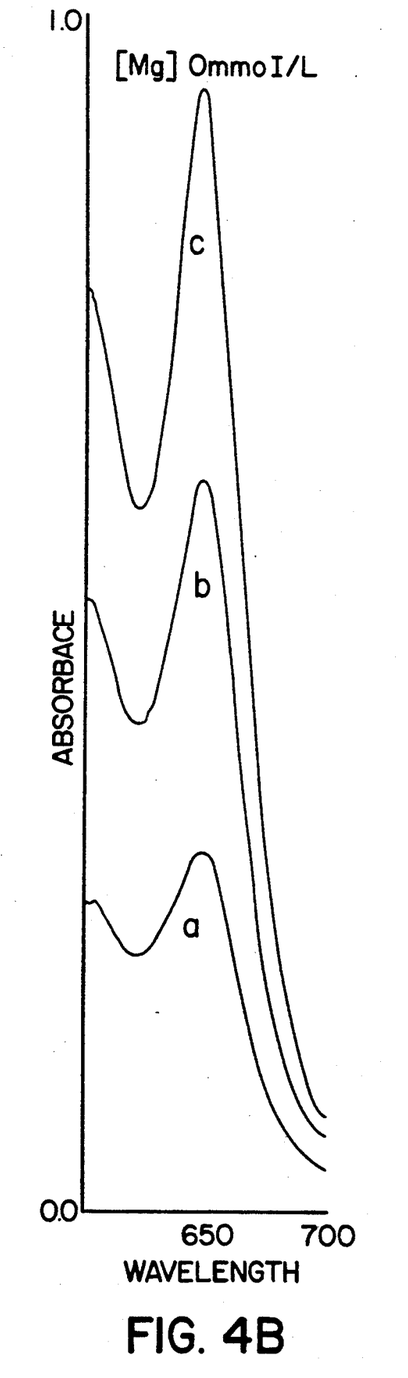
FIG. 4B shows the spectra of calcium standards contaminated with magnesium at 5 mmol/L using reagent containing 8HQS at 5 mmol/L. [ASA III]: 0.08 g/L; a. [Ca]; 1.25 mmol/L; b. [Ca]: 2.50 mmol/L; c. [Ca]: 3.75 mmol/L.

FIGS. 3A and 3B show two sets of spectra produced with reagent lacking 8HQS and calcium standards, one containing calcium (FIG. 3B) and one containing calcium contaminated with magnesium at 5 mmol/L (FIG. 3A). The spectra were obtained from 600nm to 700nm versus a reagent blank. The presence of magnesium in the reaction mixture causes an increase in absorbance for each calcium concentration (FIG. 3A). Theoretically, if enough ASA III were present in the reagent to bind all magnesium and calcium in the sample, the spectrum would represent the sum of the spectrum of the ASA III-Ca complex and spectrum of ASA III-Mg complex. Thus, a constant upward error would be expected. However, the ASA III concentration in this reagent is insufficient to bind both cations, resulting in less than a perfect constant error. FIGS. 4A and 4B show the same two sets of calcium standards used to produce FIGS. 3A and 3B but produced with reagent containing 8HQS at 5 mmol/L. The sets of spectra, in stark contrast to those in FIGS. 3A and 3B are essentially identical, confirming the effective masking effect of magnesium by 8HQS.

EXAMPLE 5

Figure 5A:
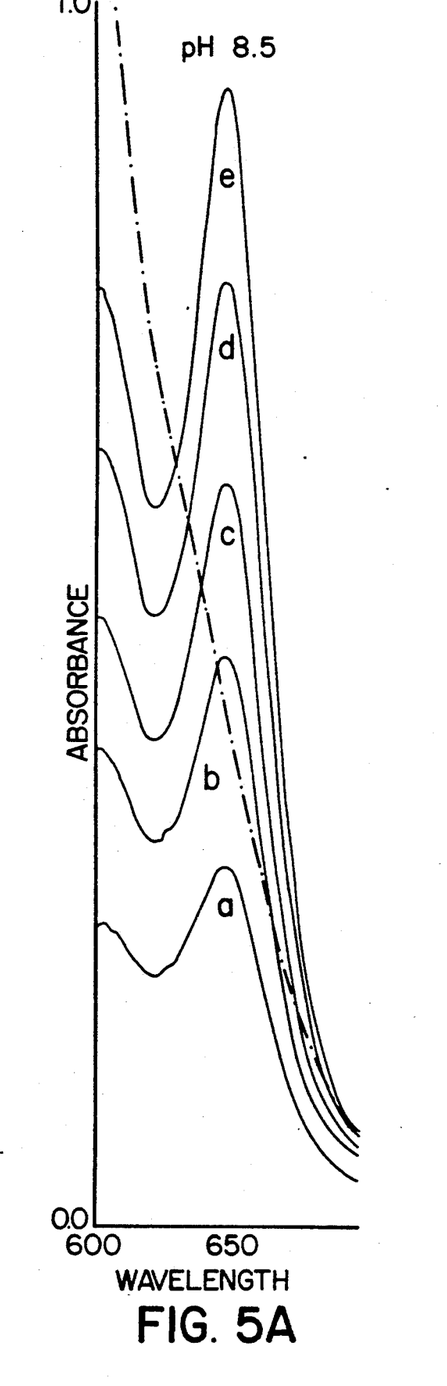
FIGS. 5A and 5B are graphs showing the spectra of 5 blank reagent (dashed lines) and a set of calcium standards (solid lines) using ASA III reagent at pH 8.5 (FIG. 5A) and ASA III reagent at pH 6.6 (FIG. 5B). a. [Ca]: 1.25 mmol/L; b. [Ca]: 1.88 mmol/L; c. [Ca]: 2.50 mmol/L; d. [Ca]: 3.13 mmol/L; ®. [Ca]: 3.75 mmol/L.
Figure 5B:
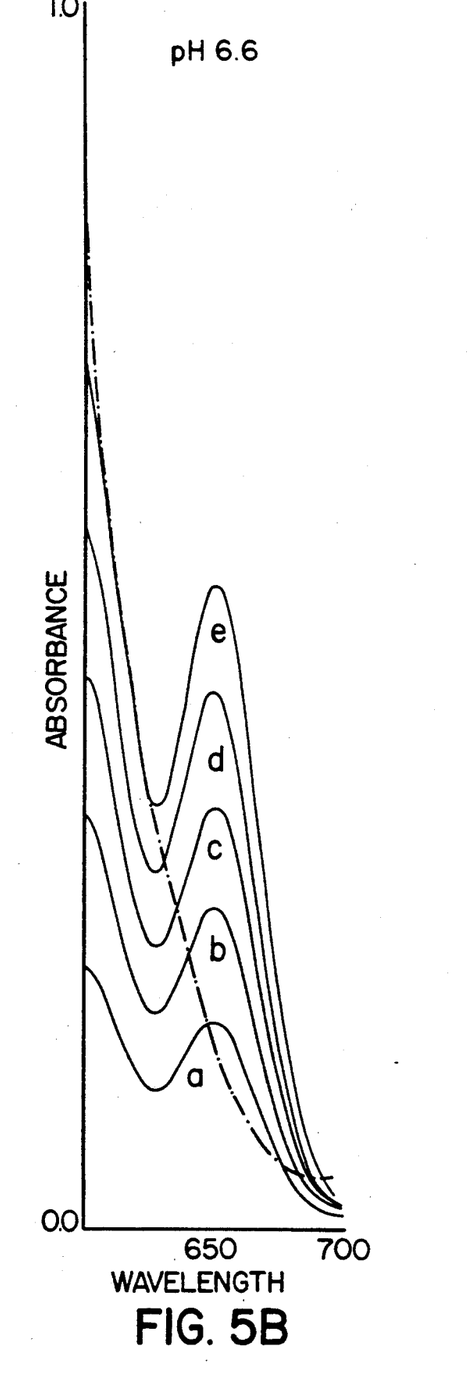

FIGS. 5A and 5B show the spectra of a set of commercial calcium standards, using acid ASA III based and alkaline ASA III based reagents, both with identical ASA III concentrations and both using a 1:100 sample to reagent ratio, blanked versus their respective blanks The acid ASA III reagent has a molar absorptivity of 13,787L/mol cm. In comparison, this reagent demonstrates a molar absorptivity of 24,507. The advantage of the alkaline ASA III reagent over the acid ASA III reagent is apparent from the increase in sensitivity.

EXAMPLE 6

Since trace metals can form complexes with ASA III, the reagent was checked for interference by copper, iron and zinc. Solutions of each were prepared from atomic absorption standard with concentrations of 1000 ug/L ([Cu]: 15.7 umol/L, [Fe]: 7.9umol/L, [Zn]: 15.3 umol/L), concentrations similar to those found in normal serum. Each standard was added to reagent and scanned versus reagent from 600 nm to 700 nm. No change was seen in the spectrum of ASA III. Next, the metal solutions were prepared with calcium set at 2.50 mmol/L. Each of these standards was added to reagent and scanned versus reagent from 600 nm to 700 nm. The spectrum of the ASA III-Ca complex for each standard containing calcium and trace metal was identical to the spectrum of the ASA II-Ca complex in the standard containing only calcium, with characteristic absorbance maxima at 650 nm and 600 nm. The peak heights of both absorbance maxima were identical for all mixtures. Finally, a 2.50 mmol/L calcium standard was contaminated by all three metal ions with the concentration of each set at 1000 ug/L. This was added to reagent and scanned versus reagent from 600 nm to 700 nm. Once again, the spectrum of the ASA III-Ca complex produced with the standard containing calcium, copper, iron and zinc was identical to the spectrum of the ASA III-Ca complex produced with the standard containing calcium alone. Thus, interference by copper, iron or zinc would not be expected under normal circumstances. Aside from 8HQS binding, iron should be too strongly bound by transferring at pH 8.5 to be removed by ASA III, and presumably that phenomenon is aided by a pH factor at the binding sites of the other trace metals.

EXAMPLE 7

Although bilirubin has little absorbance in the spectral region where the ASA III-Ca complex absorbance maximum occurs, interference by bilirubin was investigated because of its potential to oxidize easily to biliverdin. The blank reagent was mixed with a 20 mg/dl bilirubin standard (Koch, T. R. and Doumas B. T., Bilirubin, total and conjugated, modified Jendrassik-Grof method. In: Faulkner, ed. Selected methods for the small clinical chemistry laboratory. Washington, D. C.: American Association for Clinical Chemistry (1982)) and scanned versus water from 600 nm to 700 nm. No change was observed in the ASA III spectrum in the presence of bilirubin. Next, low, normal and high calcium standards were contaminated with bilirubin to give a bilirubin concentration of 20 mg/dL. The paired spectra of ASA III-Ca complexes with and without bilirubin were all identical.

EXAMPLE 8

Interference by hemolysis was studied using a hemolysate diluted to give a hemoglobin concentration of 500 mg/dL. When mixed with buffer solution and scanned versus buffer from 400 nm to 700 nm, there was no absorbance at 650 nm, the wavelength for measurement of the ASA III-Ca absorbance maximum. When a 2.50 mmol/L calcium standard was contaminated with hemoglobin having a concentration of 500 mg/dL, mixed with reagent and scanned versus reagent from 600 nm to 700 nm, as expected, there was no change in the peak height of the absorbance maximum of the ASA III-Ca complex at 650 nm.

EXAMPLE 9

Figure 6A:
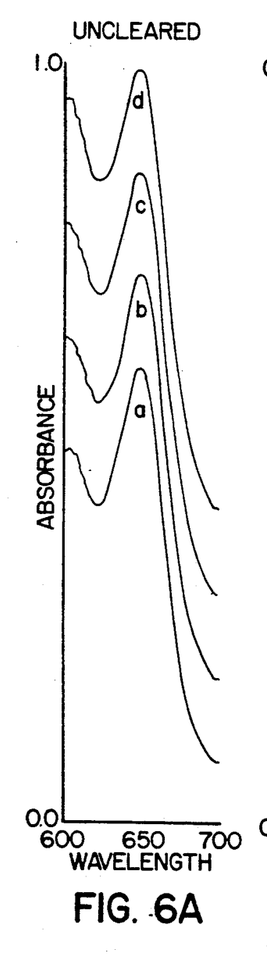
FIG. 6A shows the spectra of a 2.50 mmol/L calcium standard contaminated with increasing amount of triglyceride as Intralipid. a. [TG]: Og/L; b. [TG]: 10 g/L; c. [TG]: 20 g/L; d. [TG]: 30 g/L.

Interference by lipemia was investigated by spiking a 2.50mmol/L calcium standard with triglyceride (Intralipid TM), an intravenous lipid emulsion, to give triglyceride concentrations of 0 g/L, 10 g/L, 20 g/L and 30 g/L. Although lipid-spiked standards represent an artificial lipemia and may impart a greater degree of turbidity to the sample than does natural lipemia at those same concentrations where triglycerides are present as chylomicrons or as part of lipoproteins (Sharma, A., Artiss, J. D., and Zak, B., Microchem J 39:86-93 (1989)), these spiked standards do offer the opportunity to study the effect of varying degrees of turbidity on several calcium levels. As shown in FIG. 6A, the spectra of the ASA III-Ca complexes were increasingly distorted by the turbidity resulting from free triglyceride present in the sample. The apparent calcium was raised by about 0.5 mmol/L when the triglyceride concentration was set at 10 g/L (scan b). As the triglyceride concentration was increased further, more pronounced distortion of the spectrum of the ASA III-Ca complex was observed, with the apparent calcium concentration increased by about 1.6 mmol/L when the triglyceride concentration was set at 30 g/L (scan d). The use of a sample blank could perhaps minimize the error caused by turbidity in the calcium determination. The only other alternative to correct for lipemia is to use one of several clarification techniques (Artiss, J. D. and B. Zak Trends in Anal Chem 6:185-191 (1987)).

EXAMPLE 10

Most current off-line clarification techniques: ultracentrifugation (Musiala, T. S. and A. Dubin. Clin Chem 23:1121 (1977)), solvent extraction (Epstein, E., et al., Ann Clin Lab Sci 2:244 (1972)), detergent treatment (Helenius A. and K. Simons, Biochemistry 10:2452 (1971)), chromatography (Moorjani, S., et al., Clin Chem Acta 77:21 (1977)) and chemical precipitation (Zeppazaur, M. and S. Brishammer, Biochim Biophys Acta 94:581 (1965)) are time-consuming and not easily applied to automated instruments. The enzymic clarification method has been applied to several procedures (Morgan, B, et al., Enzymic clearing for the determination of serum calcium. Microchem J, 44:15-24 (1991); Sharma, A., et al., Clin Chim Acta 147:7-14 (1985); Artiss, J. D., et al., Clin Chim Acta 156:151-156 (1986); and Sharma, A., et al., J. Clin Chem Clin Biochem 24:57-575 (1986)) and has advantages over the above sample treatments in that it is an on-line procedure that is readily applied to automated methods. It does not require additional sample other than that ordinarily used in the method and since it is part of the reagent system, the enzymic clarification process is not cumbersome to use. The technique has been discussed in detail in other applications (Morgan, B, et al., Enzymic clearing for the determination of serum calcium. Microchem J, 44:15-24(1991); Sharma, A., et al., Clin Chim Acta 147:7-14 (1985); Artiss, J. D., et al., Clin Chim Acta 156:151-156 (1986); and Sharma, A., et al., J. Clin Chem Clin Biochem 24:571-575 (1986)) and will only be summarized here. Lipase is added to the reagent along with a detergent and fatty acid scavenger. Lipase cleaves the triglycerides present in the turbid sample into glycerol and free fatty acids liberated by this reaction are then complexed with the fatty acid scavenger, alpha-cyclodextrin, resulting in a transparent solution. For enzymic clarification with the ASA III reagent, a lipase was obtained that had maximal activity at pH 8.5-9.0. The concentration of Triton X-100 was set at 0.5 g/L, the concentration of alpha-cyclodextrin was set at 2.0 g/L and the lipase concentration was set at 1000 kU/L. Higher concentrations of enzyme can be used, but this saves little time and adds to reagents cost. When lipase was added, the reagent turned blue. When the blanks of the lipase-containing and lipase-lacking reagents were scanned from 600 nm to 700 nm versus water, the absorbance of the reagent containing lipase had increased from 0.40 to 0.46. The lipase was probably contaminated with calcium because the addition of a small amount of EGTA made the reagent turn back to red. The ASA III concentration in the reagent was increased from 0.08 g/L to 0.10 g/L to assure the dynamic range of calcium from 0 to 3.75 mmol/L.

Figure 6B:
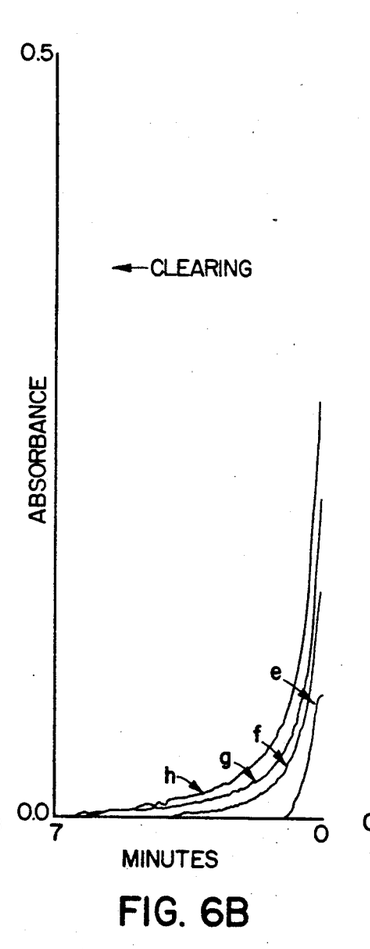
FIG. 6B shows the clarification of lipid emulsions using reagent containing lipase at 1000 kU/L, Triton X-100 at 0.5 g/L and alpha-cyclodextrin at 2 g/L. e. [TG]: 10 g/L; f. [TF]: 20 g/L; g. [TG]: 30 g/L; h. [TG]: 40 gl/L.
Figure 6C:
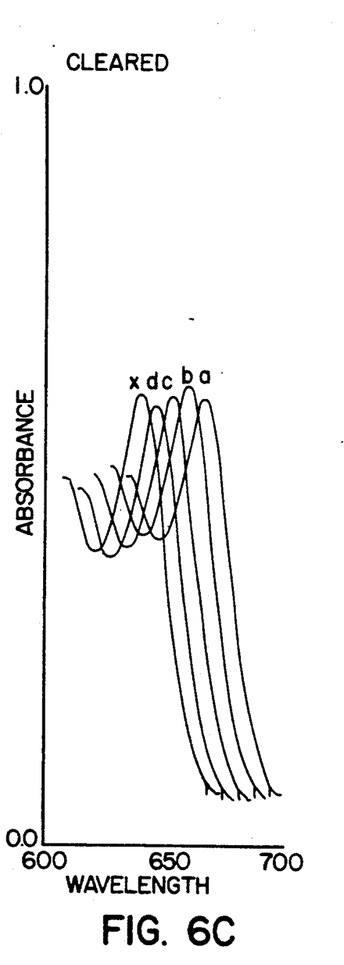

FIG. 6B shows the clarification process using reagent containing the enzymic components. Dilutions of the triglyceride concentrations ranging from 10 g/L to 40 g/L were mixed with warm reagent, placed in a spectrophotometer set at 650nm with a reagent blank, and monitored at 37° C. for 7 minutes. The sample with 10g/L (scan e) was cleared within 2 minutes. The more severely lipemic samples (scans f-h) took longer to clarify, but were cleared within the 7 minute incubation time. FIG. 6C shows the spectra of several 2.50 mmol/L calcium standards spiked with Intralipid with triglyceride concentrations ranging from 10 g/L to 40 g/L after 8 minutes of incubation at 37° C., scanned versus reagent from 600 nm to 700 nm. The absorbance maxima of the ASA III-Ca complexes overlap and lie on both sides of the absorbance of the nonturbid standard, in stark contrast to the spectra of the ASA III-Ca complexes shown in FIG. 6A, produced with reagent containing no clarification components.

EXAMPLE 11

Figure 7A:
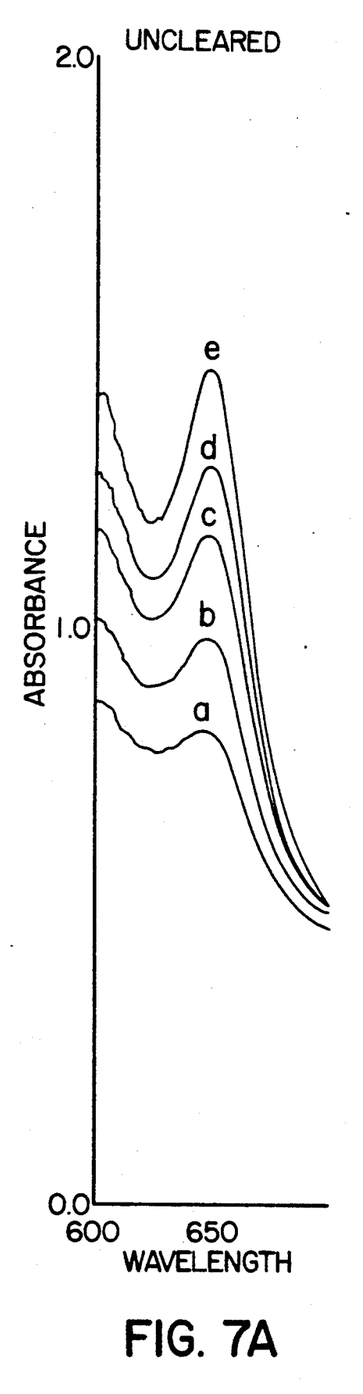
FIGS. 7A and 7B show the spectra of a set of calcium standards contaminated with triglyceride as Intralipid at 40 g/L using ASA III reagent lacking (FIG. 7A) and containing (FIG. 7B) the enzymic clarification reagents. Each was incubated at 37° C. for 8 minutes and scanned versus their respective reagent blank. a. [Ca]: 1.25 mmol/L; b. [Ca]: 1.88 mmol/L; c. [Ca]: 2.50 mmol/L; d. [Ca]: 3.13 mmol/L; e. [Ca]: 3.75 mmol/L.
Figure 7B:
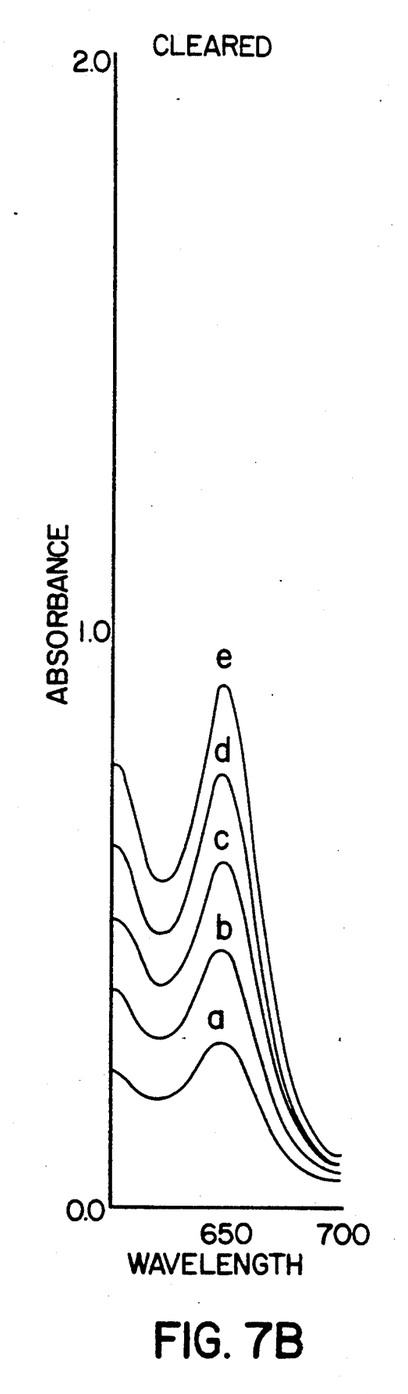

FIGS. 7A and 7B show the spectra of a set of calcium standards containing triglyceride (Intralipid ®) set at 40 g/L produced with reagents lacking (FIG. 7A) and reagents containing (FIG. 7B) the components of the enzymic clarification process. Even with this high triglyceride concentration, there is uniform clearing of all the standards, which compare favorably with the spectra shown in FIG. 5A.

EXAMPLE 12

Precision studies were performed with ASA III reagent and using Beckman Decision Control Serum, which provided three concentrations of calcium. Within-run precision data were obtained by performing the calcium determination on each sample ten times and calculating the mean, standard deviation and coefficient of variation. Between-run precision data were obtained by running each sample for twenty days. As seen in Table 1, the within-run CV's ranged from 1.1% for the low control serum to 0.4% for the high control serum.

TABLE 1
REPRODUCIBILITY STUDY

| Control Serum | Within-run precision | | | Between-run | | |
|---|---|---|---|---|---|---|
| | Mean (mmol/L) | SD (mmol/L) | CV % | Mean (mmol/L) | SD (mmol/L) | CV % |
| Low | 2.22 | 0.025 | 1.1 | 2.22 | 0.028 | 1.3 |
| Normal | 2.59 | 0.013 | 0.5 | 2.59 | 0.028 | 1.1 |
| High | 3.38 | 0.013 | 0.4 | 3.39 | 0.046 | 1.4 |

The between-run precision was slightly worse than the within-run precision for all three calcium levels. The CV for the low serum control was 1.3%, the CV for the normal serum control was 1.1% and the CV for the high serum control was 1.4%.

Figure 8:
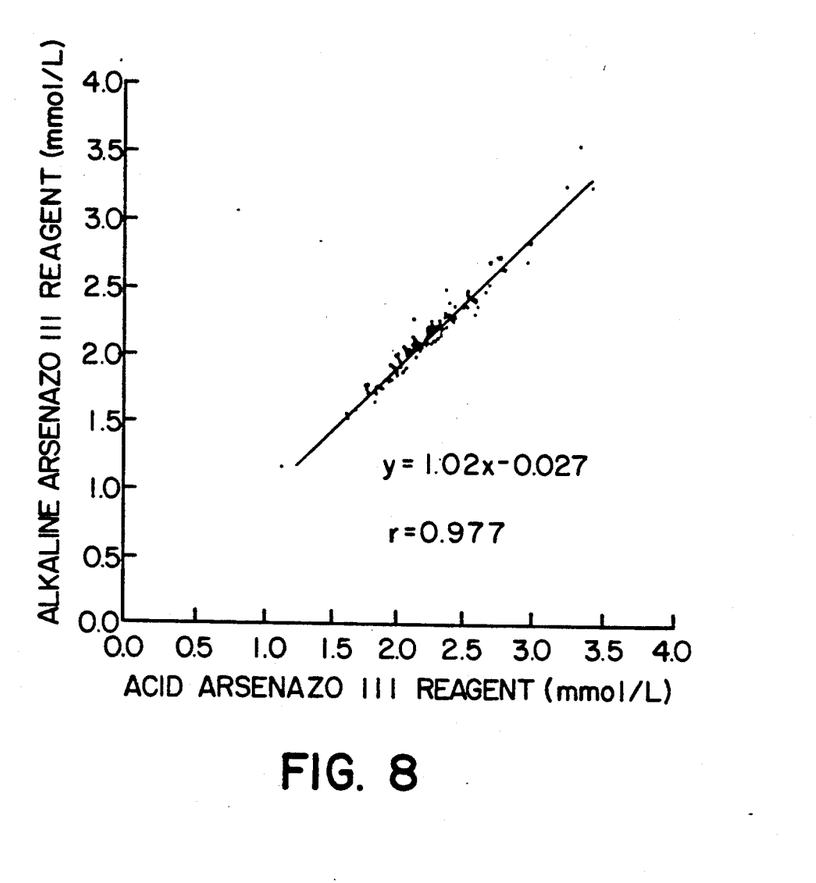
FIG. 8 is a graph showing the regression line and correlation coefficient for the comparison of acid ASA III and alkaline ASA III reagent with clear human blood sera.

A comparison study was made between the proposed method and an acid ASA III based calcium reagent. The calcium concentration of one hundred sera were analyzed by both methods. The results are plotted in FIG. 8, with the acid ASA III calcium values plotted on the X axis and alkaline ASA III calcium value plotted on the Y axis. A regression line defined by Y =1.02X −0.027 was obtained with a correlation coefficient of 0.977, demonstrating a very reasonable correlation. This reagent, when stored at room temperature, is stable for at least six (6) weeks.

It is intended that the foregoing description be only illustrative of the present invention and that the present invention be limited only by the hereinafter appended claims.

We claim:

1. A composition for determining calcium colorimetrically in the presence of magnesium which comprises in admixture in an aqueous solution having a pH between about 7.5 and 10:
   (a) arsenazo III; and
   (b) 8-hydroxyquinoline-5-sulfonate wherein the composition contains between about 0.001 and 0.08 percent by weight of the arsenazo III and between about 0.01 and 1.1 percent by weight of the 8-hydroxyquinoline-5-sulfonate and wherein calcium in the sample complexes to form a color with arsenazo III and magnesium in the sample complexes with the hydroxyquinoline to form a colorless complex.

2. The composition of claim 1 wherein the sample is serum containing calcium in an amount between about 0 and 3.75 mmol per liter.

3. The composition of claim 2 containing lipase in an amount between about 50 KU and 10,000 KU.

4. The composition of claim 3 containing alpha cyclodextrin in an amount between about 0.2 and 2.0 percent by weight.

5. The composition of claim 4 wherein the cyclodextrin is alpha cyclodextrin.

6. The composition of claim 5 wherein the composition contains between about 0.005 and 0.5 percent by weight propylene glycol p-isooctyl phenyl ether of the formula:

where n is between 9 and 10 as a dispersing agent for the composition.

7. The composition of claim 2 wherein the pH is provided by a buffer mixture of boric acid, potassium chloride and sodium hydroxide in the solution.

8. An aqueous composition having a pH between about 7.5 and 10 which comprises:
   (a) between about 0.001 and 0.8 percent by weight arsenazo III;
   (b) between about 0.01 and 1.1 percent by weight 8-hydroxy quinoline-5-sulfonate; and
   (c) between about 0.005 and 0.5 percent by weight of a compound of the formula:

where n is a number between 9 and 10.

9. The composition of claim 8 wherein the pH is provided by a buffer mixture containing boric acid, potassium chloride and sodium hydroxide.

10. An aqueous composition having a pH between about 7.5 and 10 which comprises:
   (a) between about 0.001 and 0.08 percent by weight arsenazo III;
   (b) between about 0.01 and 1.1 percent by weight 8-hydroxy quinoline-5-sulfonate;
   (c) between about 50 KU and 10,000 KU of a lipase;
   (d) between about 0.2 and 2.0 percent by weight of alpha cyclodextrin; and
   (e) between about 0.005 and 0.5 percent by weight of a compound of the formula:

where n is a number between 9 and 10.

11. The composition of claim 10 wherein the pH is provided by a buffer mixture containing boric acid, potassium chloride and sodium hydroxide.

12. In a method for a colorimetric determination of an amount of calcium in the presence of magnesium in a sample with arsenazo III as a reagent the improvement which comprises:

(a) providing an aqueous composition at a pH between about 7.5 and 10 containing arsenazo III and 8-hydroxyquinoline-5-sulfonate in amounts such that the magnesium in the sample can form a colorless complex with the hydroxyquinoline and the calcium in the sample can complex with the arsenazo III;

(b) adding the composition to the sample, wherein the calcium complex of arsenazo III produces a color with an intensity which is a function of the amount of calcium in the sample in the presence of the magnesium complexed with the hydroxyquinoline; and (c) colorimetrically determining the amount of calcium in the sample.

13. The method of claim 12 wherein the sample is human blood serum.

14. The method of claim 12 wherein the pH is provided by a boric acid, potassium chloride and sodium hydroxide buffer mixture in the solution.

15. The method of claim 12 wherein the sample is blood serum containing triglycerides and the composition contains lipase in an amount which converts the triglycerides to fatty acids and glycerol.

16. The method of claim 15 wherein the composition contains a cyclodextrin in an amount which react with the fatty acids to prevent interference by the fatty acids with the colorimetric determination.

17. The method of claim 16 wherein the cyclodextrin is alpha cyclodextrin.

18. The method of claim 17 wherein the pH is provided by a boric acid, potassium chloride and sodium hydroxide buffer mixture in the solution.

19. The method of claim 12 wherein the colorimetric determination is between 625 and 675 nm.

20. The method of claim 19 wherein the colorimetric determination is by comparing the color of the composition without the sample with the composition containing the sample.

21. The method of claim 12 wherein the sample is human blood serum and wherein the range of calcium in the serum detected is between about 0 and 3.75 mmole per liter.

* * * * *

UNITED STATES PATENT AND TRADEMARK OFFICE
CERTIFICATE OF CORRECTION

PATENT NO. : 5,215,922

DATED : June 1, 1993

INVENTOR(S) : Joseph D. Artiss, Bradley R. Morgan and Bennie Zak

It is certified that error appears in the above—identified patent and that said Letters Patent is hereby corrected as shown below:

Column 1, line 32, "colorimetry" should be --colorimetric--.

Column 2, line 55, "i mmol" should be --1 mmol--.

Column 2, line 64, "[Ca925 mmol" should be --[Ca]: 1.25 mmol--.

Column 3, line 10, "®" should be --e.--.

Column 3, line 23, "Fig. 6°C" should be --Fig. 6C--.

Column 4, line 63, a period --.-- should be inserted after "results" and before "Usually".

Column 6, line 12, after "liter" a colon --:-- should be inserted.

Column 6, line 14, "Triton X-1000", should be --Triton X-100--.

UNITED STATES PATENT AND TRADEMARK OFFICE
CERTIFICATE OF CORRECTION

PATENT NO. : 5,215,922

DATED : June 1, 1993

INVENTOR(S) : Joseph D. Artiss, Bradley R. Morgan and Bennie Zak

It is certified that error appears in the above—identified patent and that said Letters Patent is hereby corrected as shown below:

Column 6, line 49, a period --.-- should be inserted after "established" and before "In".

Column 8, line 35, a period --.-- should be inserted after "blanks" and before "The".

Column 8, line 47, "7.9 umol" should be --17.9 umol--.

Column 10, line 21, "24:57-575" should be --24:571-575--.

Column 10, line 68, "10g/L" should be --0g/L--.

Column 11, line 43, "13%" should be --1.3%--.

Signed and Sealed this

Eighth Day of February, 1994

Attest:

BRUCE LEHMAN

*Attesting Officer*    *Commissioner of Patents and Trademarks*